United States Patent
Seligman

(10) Patent No.: US 7,120,500 B1
(45) Date of Patent: Oct. 10, 2006

(54) BATTERY MONITOR AND POWER DEMAND ADJUSTER

(75) Inventor: Peter Seligman, Essendon (AU)

(73) Assignee: Cochlear Limited, Lane Cove (AU)

( * ) Notice: Subject to any disclaimer, the term of this patent is extended or adjusted under 35 U.S.C. 154(b) by 0 days.

(21) Appl. No.: 10/257,170

(22) PCT Filed: Apr. 11, 2000

(86) PCT No.: PCT/AU00/00305

§ 371 (c)(1),
(2), (4) Date: Dec. 23, 2002

(87) PCT Pub. No.: WO01/78449

PCT Pub. Date: Oct. 18, 2001

(51) Int. Cl.
*A61N 1/08* (2006.01)

(52) U.S. Cl. .......................... 607/55; 607/29

(58) Field of Classification Search ............ 607/1, 607/2, 29, 34, 55–57; 307/126, 130; 320/135, 320/136; 324/433
See application file for complete search history.

(56) References Cited

U.S. PATENT DOCUMENTS

| | | | |
|---|---|---|---|
| 4,120,307 A * | 10/1978 | Jirak et al. | 607/29 |
| 4,590,941 A * | 5/1986 | Saulson et al. | 607/34 |
| 5,457,365 A * | 10/1995 | Blagaila et al. | 318/430 |
| 5,668,465 A | 9/1997 | May | |
| 5,773,961 A | 6/1998 | Cameron et al. | |
| 5,869,970 A | 2/1999 | Palm et al. | |
| 5,870,685 A | 2/1999 | Flynn | |
| 5,963,255 A * | 10/1999 | Anderson et al. | 348/372 |

FOREIGN PATENT DOCUMENTS

| | | |
|---|---|---|
| EP | 0653826 A2 | 5/1995 |
| JP | 06-178456 A | 6/1994 |
| JP | 10-108385 A | 4/1998 |
| JP | 10-108385 A2 | 4/1998 |
| JP | 10-108387 A | 4/1998 |
| WO | WO 97/01314 | 1/1997 |

OTHER PUBLICATIONS

International Search Report; dated Jun. 26, 2000; for International Patent Appln No. PCT/AU00/00305; Published Oct. 18, 2001 (WO 01/78449); Inventor; Seligman, Peter.
Written Opinion; for International Patent Appln No. PCT/AU00/00305; dated Nov. 29, 2001; Inventor: Seligman, Peter.
International Preliminary Examination Report; dated Feb. 8, 2002: for International Patent Appln No. PCT/AU00/00305; Inventor: Seligman, Peter.

* cited by examiner

*Primary Examiner*—Robert E. Pezzuto
*Assistant Examiner*—Kristen Mullen
(74) *Attorney, Agent, or Firm*—Jagtiani + Guttag

(57) ABSTRACT

A system for monitoring and controlling power demands in devices with DC power supplies. In response to a detected decline in voltage levels, the device reduces power demands of the device, in one or more stages before powering down entirely. This approach has application to battery powered devices, particularly fro medical applications such as cochlear implants.

10 Claims, 3 Drawing Sheets

BATTERY MONITOR AND POWER DEMAND ADJUSTER

TECHNICAL FIELD

The present invention relates generally to devices powered by energy storage arrangements, and in particular but not exclusively to prostheses and stimulation devices powered by batteries.

BACKGROUND ART

Many devices are powered by electrochemical cells, particularly devices for medical use. Examples of such devices include hearing prostheses, neural stimulators, pacers, drug pumps and other devices. Increasingly, these devices use digital processing systems, rather than analog systems which were the standard prior art technique. One feature of digital systems is that the processor used will generally require a certain minimum voltage to operate effectively. If this is not present, the device will fail erratically. To avoid this, a system shutdown voltage level is generally used, at which level the device shuts itself down. This level is often set well above the actual minimum level, to avoid the possibility of error from a dubious power supply. In contrast, prior art analog systems generally fail gradually, with progressively less performance delivered as less voltage is available from the battery. Accordingly, the user has generally more warning of impending device failure.

To take the example of cochlear implants, modern speech processors are controlled by and process speech using a microprocessor. The speech processor also provides power to an induction loop, which via an inductive coupling supplies power and data to an implanted receiver stimulator unit. Although in principle any suitable battery could be used to provide power to such systems, the zinc-air cell is the preferred power source. Such cells are also commonly used for applications such as external hearing aids.

Zinc air cells have several practical advantages. They have a very high energy density, and so can supply a device's requirements for a relatively long period of time relative to their size and weight. They also have a relatively constant power output through most of their life, so that there is little risk of dangerous rapid discharge, for example by shorting. However, if they experience a heavy load, then it is common for the voltage to temporarily sag.

Conventionally, such devices have employed a battery monitor arrangement, whereby the voltage is monitored and if it falls below a certain level, the device is shut down. Such voltage levels are often set at a value which corresponds to a relatively high power demand, so as to prevent anomalous operation due to under voltage. As a result, if even a relatively new battery is subjected to adverse conditions, for example a period of heavy load, the cell voltage may fall below the pre-defined cut-off level and the processor will be shut down. In the field of Cochlear implants such an event is inconvenient and has potentially serious implications. After shut-down, the user must reset the speech processor by re-starting it, and hence the user is disconnected for a time from their hearing environment. Similar problems can arise with other battery powered digital systems, where short term conditions cause a temporary reduction in the voltage of the power supply.

It is an object of the present invention to provide an improved battery monitoring arrangement in order to improve the performance of battery powered devices.

SUMMARY OF THE INVENTION

The present invention provides, broadly, for a device in which battery performance is monitored, and in which the power demands of a device are reduced to match the available battery power. This allows for what may be called graceful failure, rather than complete shut-down at an arbitrary level.

In the case of a cochlear implant, one implementation is to introduce a series of battery voltage trigger levels, at or below which levels aspects of processor performance are downgraded. A preferred implementation progressively reduces the stimulation rate as the battery voltage declines, until it ultimately reaches a shut-down level. However, if the battery voltage increases before shut-down level is achieved, the stimulation rate is progressively increased to normal levels. This allows the device to cope with a degree of voltage sag without ceasing to function.

Alternative responses to a reduction in voltage for a cochlear implant implementation may include a change in the speech processing strategy, or other changes to reduce power requirements. In other devices, the performance of the device may be reduced by changes in the operation of processors or other elements, without shutting down the system. These alternatives may be used separately or in combination.

Whilst the present invention has particular advantages for zinc-air cells, the principle has application to other battery-powered digital devices, especially devices whose continued function, even at a reduced level of performance, is important.

BRIEF DESCRIPTION OF DRAWINGS

An implementation of the present invention will now be described with reference to the accompanying figures, in which.

DESCRIPTION

The present invention will be described with particular reference to a speech processor unit for a cochlear implant system. However, it will be appreciated that the present invention has application to other devices using a battery to power a digital device, with modifications appropriate to the application as would be apparent to those skilled in the art. The implementation is intended to illustrate the invention's application to a particular situation, being a speech processor for an intracochlear implant.

Figure 1:
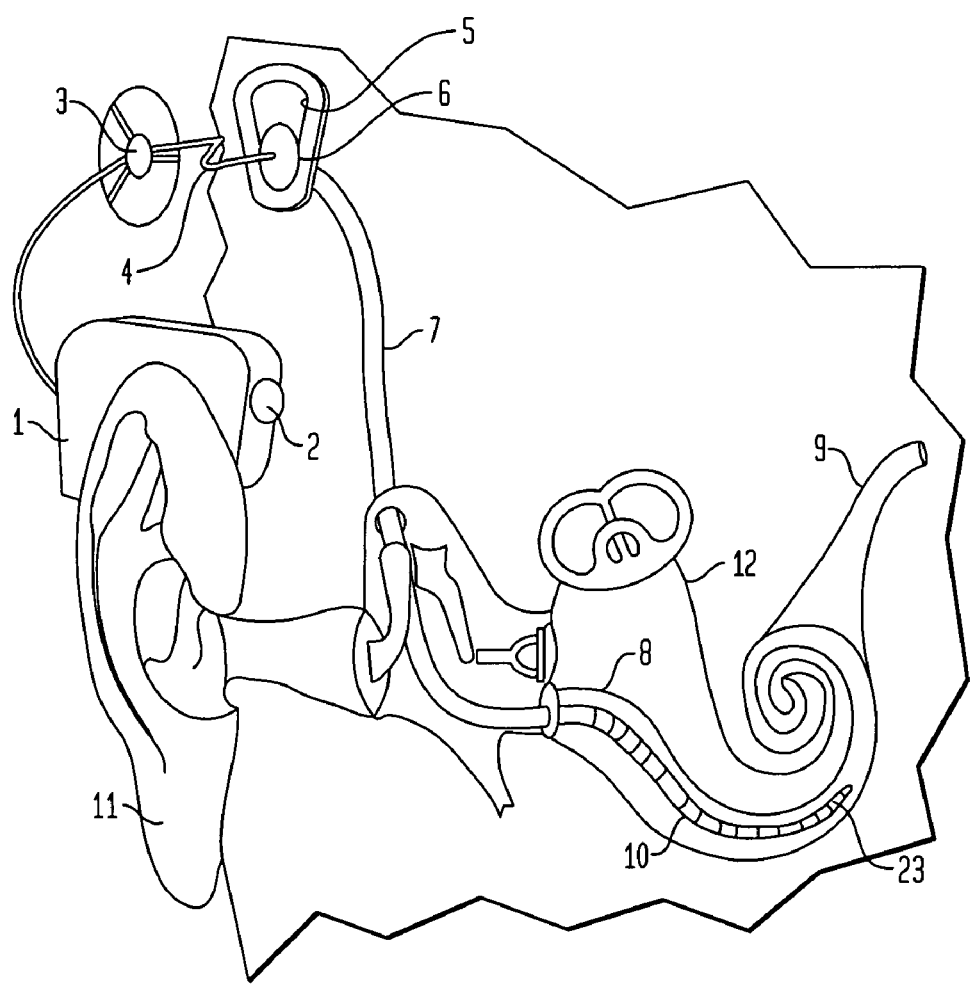
FIG. 1 is a schematic illustration of a conventional intra-cochlear implant system.

Referring to FIG. 1, a typical cochlear implant device is shown. It will be appreciated that such an arrangement is well known in the art, and that the illustration and the following discussion are intended purely to provide a context for the present invention. From this figure can be seen the external component, including a speech processor 1, and an internal component including an implanted receiver and stimulator unit 6. The external component further includes a microphone 2 which is shown integral with the speech processor 1. The speech processor is in this illustration constructed and arranged so that it can fit behind the outer ear 11. Alternative versions may be worn on the body.

Attached to speech processor 1 is a transmitter coil 3 which transmits the electrical signals to the implanted unit 6 via an RF link 4.

The implanted component includes a receiver coil 5 for receiving power and data from coil 3. A cable 7 extends from the implanted device 6 to the cochlea 12 and terminates in an electrode array 10. The signals thus received are applied by the array 10 to the basilar membrane 8 thereby stimulating the auditory nerve 9. The operation of the device shown in FIG. 1 is described, for example, in the applicant's U.S. Pat. No. 4,532,930, the disclosure fo which is hereby incorporated by reference.

Thus, the RF link, which is in turn powered by the speech processor 1, provides power and data to the implanted device 6. The speech processor also processes sound signals received by microphone 2, so as to send appropriate instructions for stimulation to the implanted device 6. The precise details of speech processing are not necessary for an understanding of the present invention, and the skilled worker in the art will be aware that many such schemes have been used and proposed. What is pertinent is that some of these schemes, and their modes of operation, consume variable levels of power. For example, a higher rate of stimulation using a given processing scheme will generally consume more power.

A cochlear implant device such as that illustrated in FIG. 1 may be powered by zinc-air cells. Conventionally, zinc-air cells are used to power speech processor units, especially behind the ear type processors. The technology of these cells is such that even though the cell capacity is very high, only a limited current is available.

In existing devices, a battery monitor arrangement is provided in the speech processor 1. The monitor measures the output voltage from the battery, and if the voltage falls below a certain level, the monitor sends a signal to the processor which shuts down the processor. Thus a combination of adverse factors can cause the cell voltage to drop, causing the low voltage trip to operate, switching the processor off. This may happen even if the cells are new, causing unnecessary inconvenience to the patient.

According to the present invention, this problem can be overcome by reducing the power requirements of the system when the voltage drops a certain level. One way to reduce power requirements is to lower the stimulation rate being applied by the implant. Effectively power consumption is proportional to rate (apart from a small quiescent current). Although stimulation rate can have an effect on patient speech recognition performance, it is likely that the circumstances leading to such a rate reduction are situations of severe background noise such as a noisy train. When the adverse situation has passed, the rate returns to the normal programmed rate.

According to one implementation of the present invention, the stimulation rate is modulated at a rate determined by the cell voltage. When the cell voltage is above a predetermined threshold level the stimulation rate is at a pre-set normal value. When the cell voltage falls below a second predetermined threshold level, the low-voltage alarm is triggered and the speech processor shuts down in the same fashion as a prior art speech processor.

The cell voltage may be determined by various mechanisms. An analog or digital voltmeter device could be used, a software function within the processor, or simply an analog circuit arrangement responsive to certain voltage levels. Any suitable means may be used, as would be understood by those skilled in the art.

The two thresholds create an intermediate range of cell voltages within which the cell or cells are still capable of supporting some functionality, but not the full operational mode. Within this range the speech processor enters a reduced functionality mode. In one embodiment this would involve the speech processor switching to a low-power mode. It is preferable, however, that the speech processor operate at a stimulation rate which is determined by the measured cell voltage, as shown in FIG. 2.

Figure 2:
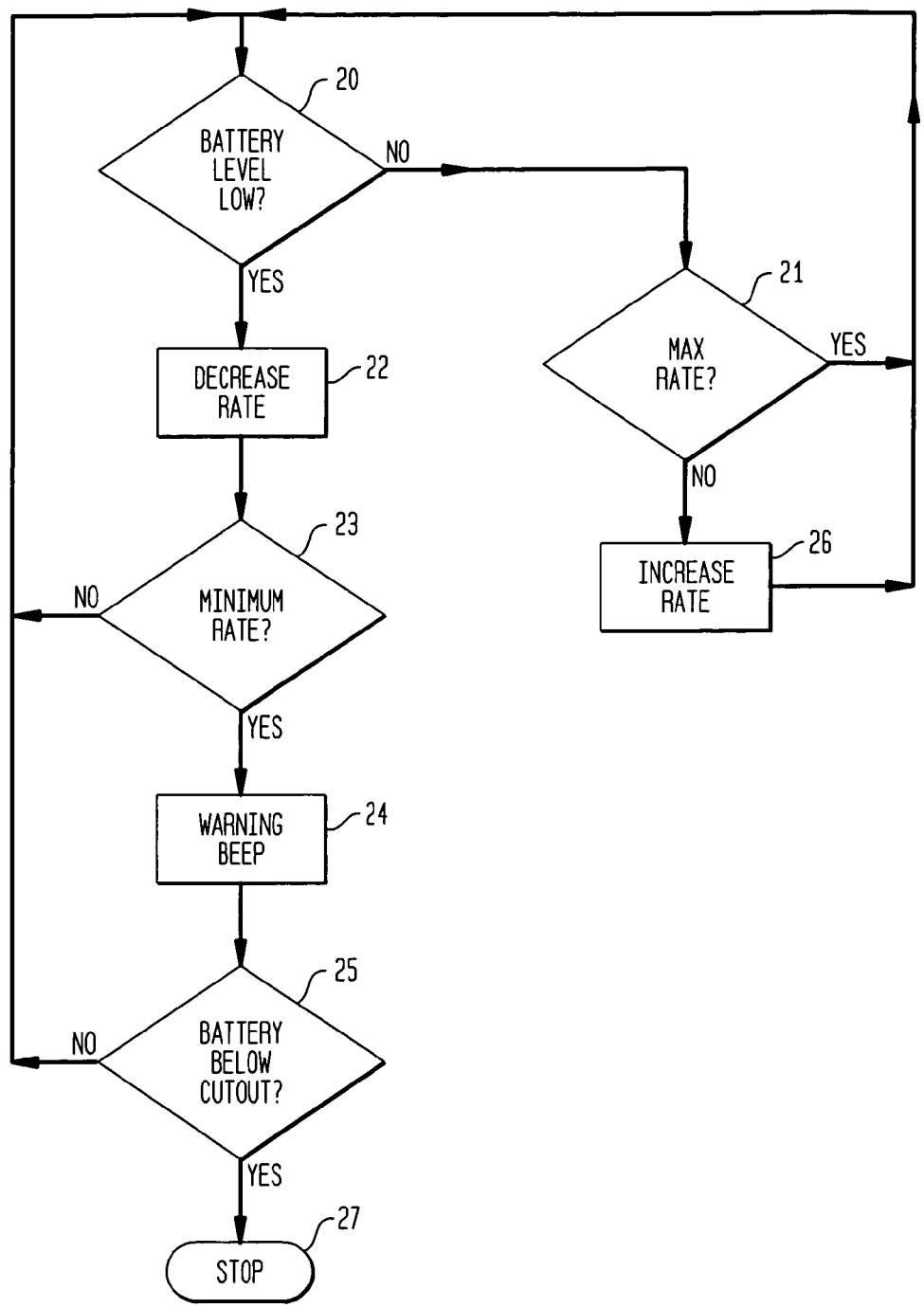
FIG. 2 is a flow chart illustrating the operation of the inventive system.

Referring to FIG. 2, a flowchart illustrating one implementation of the invention is shown. At box 20, the process determines if the battery voltage level is low, that is, below a first predetermined value. If it is, then the stimulation rate is decreased at box 22. If the value at box 20 is not below a first predetermined value, then box 21 determines if the processor is operating at its maximum stimulation rate. If it is, then the process loops back to box 20. If the rate is not at maximum, the rate is increased by a predetermined amount in box 26 and the process again loops back to box 20.

If the stimulation rate has been decreased at box 22, box 23 determines if the stimulation rate is at the preset minimum rate—in other words, if it is at the minimum tolerable stimulation rate. If not, then the process loops back to box 20. If it is at minimum rate, box 24 instructs a warning beep to be provided to the user, so that the user is aware that the processor may be shut down shortly. Box 25 then tests if the battery level is below a second predetermined threshold level. If it is, then the processor is stopped at box 27 and the speech processor shuts down. If it is not at the cutoff level, the process loops back to box 20.

It will be appreciated that alternative responses to progressively lower levels could be readily implemented in a speech processor. One alternative would be to switch at a certain level to an alternative speech processing strategy, which requires less power, or provides better speech percepts at low stimulation rates. For example, at a first predetermined level the very low battery response may be to switch to another processing strategy, which copes better with progressive stimulation rate reduction than the normal strategy. Another option, for example in a processor which uses a selection of channels from a filter arrangement as a basis for stimulation, may be to reduce the number of channels processed by the filter and/or to reduce the number of channels selected as the basis for stimulation. Other alternative strategies could be used to reduce power requirements in different applications, as would be apparent to those skilled in the art. Combinations of these approaches could be used.

Preferably the method is implemented as a closed loop method. If the voltage drops below the higher threshold, the rate begins to slow gradually by introducing an additional wait period at the end of a count which determines the stimulation rate. If the voltage rises again, the wait is gradually reduced. As a result, the processor stimulates at a rate which keeps the cell voltage at close to the higher threshold. If the load increases or the cell output decreases, the rate lowers further until it is unable to keep the cell voltage at the high threshold. The result is that the voltage continues to drop until the low threshold is reached. As this point the processor cuts out.

The stimulation rate could be determined by a measure of cell voltage which incorporates some time information. This could be, for example, the average cell voltage over the last 5 minutes.

Figure 3:
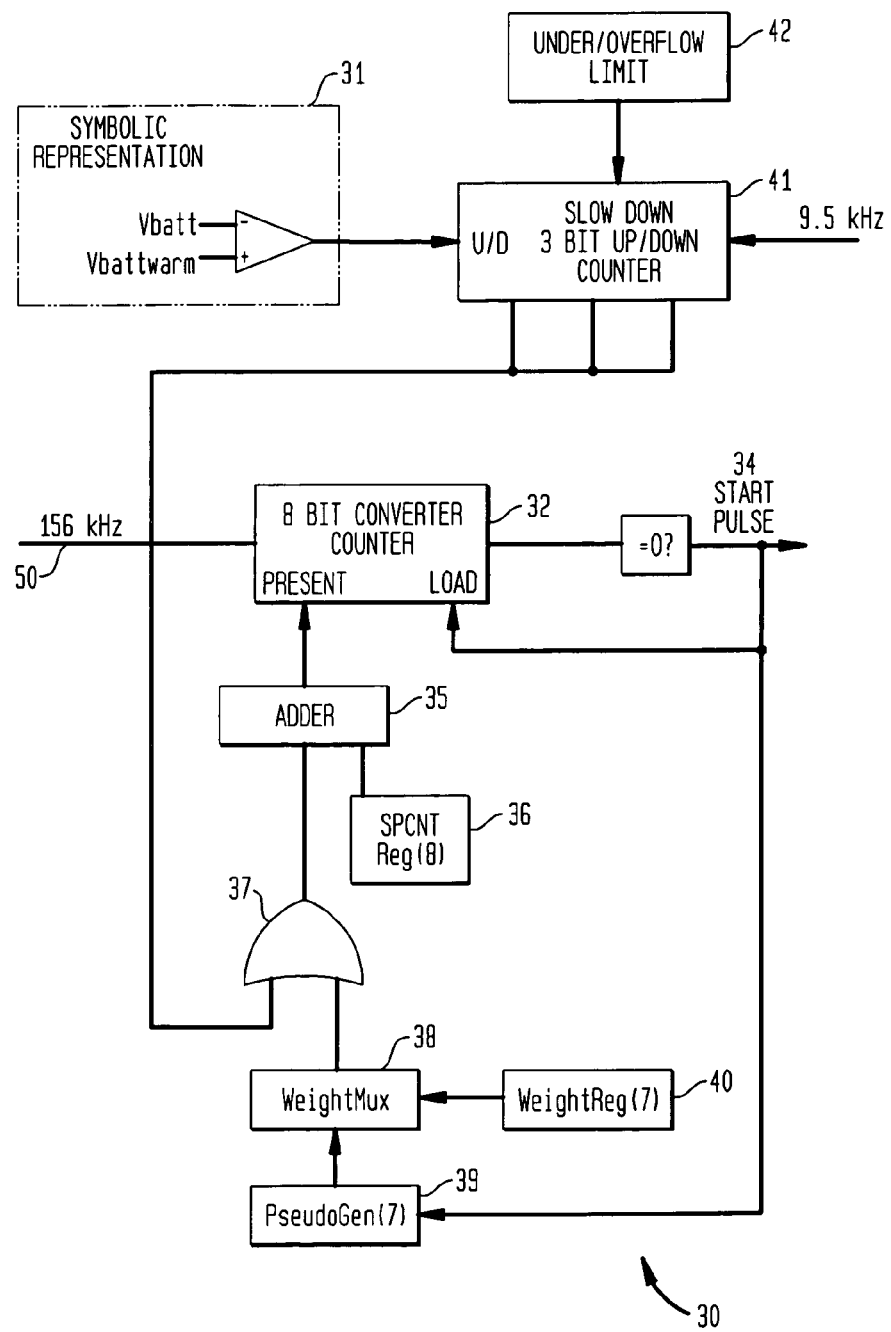
FIG. 3 is a schematic diagram of a central circuit utilising the present invention.

FIG. 3 illustrates a practical implementation of the present invention for a cochlear implant. The illustrated system is a start pulse 34 generator 30, which generates pulses for commencing each cycle of stimulation generation by the speech processor. The pulse rate is set by a counter 32 which counts 6.4 us ticks received on line 50. The count is set by register SPCNT 36. At count 0 the counter 32 is automatically reloaded by the output adder 35. Input to adder 35 is the SPCNT word from register 36, and the output from a 7 bit pseudo random generator 39 with bits masked by Weight-Mux 38 as indicated by the weight register 40.

In order to provide the features of the present invention, the low battery warning operation is altered so that when the threshold is encountered the start pulse counter is increased. The wait is increased by modifying the top 3 bits of the 7 bit WEIGHT register 40 with a count from a 3 bit SLOW-DOWN counter 41. The output of this result 37 is added to SPCNT 36 to provide the input to counter 32.

The SLOWDOWN counter 41 operates on the detection of the Batwarn signal from box 31. This is when the battery voltage drops below a first predetermined level, the Batwarn setting. When the battery voltage has dropped below this level, the SLOWDOWN counter is clocked up at the rate of 9.5 Hz. If the battery voltage is above the Batwarn level, the counter is clocked down at 9.5 Hz. At each end of its range, the counter is prevented from overflowing by box 42. By this means, the period of START PULSE (SP) is increased slowly by $16*6.4=102.4$ μs steps from a minimum of 0 to a maximum of $7*102.4=716.8$ μs in addition to the value set. Assuming that the SP rate is typically set to 1500 Hz, i.e. with a period of 667 μs, this means that as the battery voltage sinks below the Batwarn level, the pulse rate is gradually slowed down to approximately half of its normal rate. If the power demands lessen, the rate will increase again to the normal rate of the start pulse counter.

Jitter in the start pulses can be used in the lower 4 or 5 bits. If 5 bits of jitter are used, the period will be for example 567–767 μs for no slow down, then a bit D4 is over-ridden by the SLOWDOWN counter, the jitter will be 667–767 μs. When bit D5 is set by the counter, the jitter will be 767–967 μs etc. If 4 bits of jitter are used, the sequence will be 667, 769, 871 μs+/−51 μs. In this way the range of jitter is reduced under some circumstances but there is a gradual progression in the overall rate change.

To give the patient a warning of low battery, a beep is generated when the SLOWDOWN counter first reaches its maximum count It will be understood that the above example is merely one embodiment of the present invention, and that variations and additions are possible within the broad scope of the inventive concept, as will be apparent to those skilled in the art.

The invention claimed is:

1. A method of operating a speech processor for a cochlear prosthesis, said processor being powered by a DC power source and including monitoring means for measuring the output voltage of said power source, said processor being arranged to implement speech processing strategies and stimulation strategies, and to permit one or more of the speech processing strategy, the stimulation strategy, and stimulation rate to be changed, said processor further includes control means responsive to said monitoring means, said method comprising:

measuring the output voltage of said power source;

reducing power demands of said device when said measured output voltage falls below a first predetermined voltage level, by control means, comprising, altering one or more of the speech processing strategy, stimulation strategy and stimulation rate implemented by said processor; and shutting down the processor when said measured output voltage falls below a second predetermined voltage level, wherein said second level is lower than said first level.

2. The method according to claim 1, wherein said altering one or more of the speech processing strategy, stimulation strategy and stimulation rate implemented by said processor comprises one or more of:

reducing the stimulation rate, reducing a number of sound channels selected from a filter arrangement serving as basis for stimulation, reducing the number of channels processed by said filter arrangement, and selecting an alternative speech processing strategy.

3. The method according to claim 1, wherein said method further comprises:

progressively reducing the power demands of said device when said measured output voltage falls between said first and second predetermined levels, comprising: further altering one or more of the speech processing strategy, the stimulation strategy and the stimulation rate implemented by said processor.

4. The method according to claim 3, wherein said method further comprises:

progressively increasing the power demands of the device, so that in one or more stages the device is restored to its normal operating mode, when the power demands of said device have previously been lowered, and the output voltage has increased.

5. The method according to claim 1, wherein said method further comprises:

reducing gradually the stimulation rate of said processor when the output voltage falls below said first predetermined level, and increasing gradually the stimulation rate when said output voltage increases.

6. A speech processor for a cochlear prosthesis, said processor being powered by a DC power source and including monitoring means for measuring the output voltage of said power source, said processor being arranged to implement speech processing strategies and stimulation strategies and to permit one or more of the speech processing strategy, the stimulation strategy, and stimulation rate to be changed, the speech processor comprising:

control means, responsive to said monitoring means, for altering one or more of the speech processing, stimulation strategy and stimulation rate implemented by said processor, said control means comprising:

means for altering one or more of the speech processing strategy, stimulation strategy and stimulation rate implemented by said processor so as to reduce power requirements of the device when the output voltage level of said power source falls below a first predetermined level, and means for shutting down the processor when the output voltage level detected by said monitoring means falls below a second predetermined level, said second level being lower than said first level.

7. The speech processor of claim 6, wherein said means for altering one or more of the speech processing strategy, stimulation strategy and stimulation rate implemented by said processor comprises:

means for reducing the stimulation rate, means for reducing a number of sound channels selected from a filter arrangement serving as basis for stimulation, means for reducing the number of channels processed by said filter arrangement, and means for selecting an alternative speech processing strategy.

8. The speech processor of claim 7, wherein when the output voltage is between said first and second predetermined levels, said altering means progressively reduces the power demands of said processor by further altering one or more of the speech processing strategy, the stimulation strategy and the stimulation rate implemented by said processor.

9. The speech processor of claim 8, wherein when said control means has previously reduced the power demands of said device, and said monitoring means determines that the output voltage has increased, said control means progressively increases the power requirements of the device, so that in one or more stages the device is restored to its normal operating mode.

10. The speech processor of claim 6, wherein when the output voltage falls below said first predetermined level, said altering means gradually reduces the stimulation rate of said processor to a predefined minimum level, and when said output voltage increases, said altering means gradually increases the stimulation rate.

* * * * *